(12) United States Patent
Liu et al.

(10) Patent No.: US 7,219,021 B2
(45) Date of Patent: May 15, 2007

(54) MULTIPLE WIRELESS SENSORS FOR DIALYSIS APPLICATION

(75) Inventors: James Z T Liu, Hudson, NH (US); Gautham Ramamurthy, Bangalore (IN); Alistair D. Bradley, Dublin, OH (US); James D. Cook, Freeport, IL (US); Stephen R. Shiffer, Xenia, OH (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/317,706

(22) Filed: Dec. 24, 2005

(65) Prior Publication Data

US 2007/0061089 A1    Mar. 15, 2007

Related U.S. Application Data

(63) Continuation-in-part of application No. 11/242,271, filed on Oct. 3, 2005, and a continuation-in-part of application No. 11/226,085, filed on Sep. 13, 2005, now Pat. No. 7,181,975.

(51) Int. Cl.
*G01F 17/00* (2006.01)
(52) U.S. Cl. ...................................... 702/50
(58) Field of Classification Search .................. 702/50; 600/549, 561; 73/718; 604/4.01; 370/278; 324/318; 435/4; 343/895
See application file for complete search history.

(56) References Cited

U.S. PATENT DOCUMENTS

| | | | |
|---|---|---|---|
| 4,660,568 A * | 4/1987 | Cosman | 600/561 |
| 4,926,125 A * | 5/1990 | Roemer | 324/318 |
| 6,179,586 B1 | 1/2001 | Herb et al. | 417/480 |
| 6,619,133 B1 | 9/2003 | Goshoo et al. | 73/754 |
| 6,695,806 B2 | 2/2004 | Gelfand et al. | 604/6.09 |
| 6,726,923 B2 | 4/2004 | Iyer et al. | 424/443 |
| 6,730,220 B2 | 5/2004 | McCartney | 210/241 |
| 6,755,976 B2 | 6/2004 | Rosenqvist et al. | 210/646 |
| 6,811,707 B2 | 11/2004 | Rovatti et al. | 210/739 |
| 6,861,266 B1 | 3/2005 | Sternby | 436/178 |
| 6,887,214 B1 | 5/2005 | Levin et al. | 604/6.11 |
| 6,901,807 B1 | 6/2005 | Wang et al. | 73/718 |
| 6,923,069 B1 | 8/2005 | Stewart | 73/723 |
| 6,952,963 B2 | 10/2005 | Delnevo | 73/290 B |
| 2004/0019312 A1 * | 1/2004 | Childers et al. | 604/4.01 |

(Continued)

FOREIGN PATENT DOCUMENTS

WO    WO 02/22187 A2    3/2002

(Continued)

*Primary Examiner*—John Barlow
*Assistant Examiner*—Xiuqin Sun
(74) *Attorney, Agent, or Firm*—Kermit D. Lopez; Luis M. Ortiz

(57) ABSTRACT

A sensor system for dialysis applications includes a plurality of pressure sensors, wherein each pressure sensor can be provided as an LC type sensor, and/or an RLC type sensor. Each sensor among the plurality of pressure sensors can be inductively coupled with a respective antenna among a plurality of antennas for the wireless transmission of pressure data. A dialysis machine is generally connected to the plurality of antennas, wherein the plurality of pressure sensors monitors pressure during operation of the dialysis machine to generate pressure data that is wirelessly transmitted to at least one antenna among the plurality of antennas.

21 Claims, 8 Drawing Sheets

U.S. PATENT DOCUMENTS

2005/0070811 A1* 3/2005 Crowley .................... 600/549
2005/0103112 A1* 5/2005 Pedersen et al. .............. 73/718
2005/0163063 A1* 7/2005 Kuchler et al. ............ 370/278
2005/0202397 A1* 9/2005 Zhang et al. ................. 435/4

FOREIGN PATENT DOCUMENTS

WO     WO 02/085040 A1    10/2002
WO     WO 2004/078463 A1    1/2004

* cited by examiner

MULTIPLE WIRELESS SENSORS FOR DIALYSIS APPLICATION

CROSS-REFERENCE TO RELATED PATENT APPLICATIONS

This patent application is a Continuation-In-Part (CIP) of U.S. patent application Ser. No. 11/242,271, entitled "Wireless Pressure Sensor and Method Forming the Same," which was filed on Oct. 3, 2005, and is incorporated herein by reference in its entirety. This patent application is also a Continuation-In-Part (CIP) of U.S. patent application Ser. No. 11/226,085, entitled "Wireless Capacitance Pressure Sensor," which was filed on Sep. 13, 2005, now U.S. Pat. No. 7,181,975, and is incorporated herein by reference in its entirety.

TECHNICAL FIELD

Embodiments are generally related to sensing devices and methods. Embodiments are also related to wireless sensors. Embodiments are additionally related to dialysis applications and pressure sensors for use in monitoring pressure during a dialysis application.

BACKGROUND OF THE INVENTION

Sensors are utilized in a number of applications, including various medical, commercial and industrial applications. For example, it is often necessary to monitor pressure and/or to detect flow rates in medical applications and processes.

One area where pressure sensors, for example, find particular usefulness is in the area of hemodialysis applications. In such medical procedures, a dialysis machine is utilized to clean wastes from the blood after the kidneys have failed. The blood travels through tubes to a dialyzer, a machine that removes wastes and extra fluid. The cleaned blood then goes back into the body.

A known-type dialysis machine comprises a first blood circulation circuit and a second circulation circuit for the dialysate liquid. The first circuit and the second circuit are connected to a filter for conveying, respectively, the blood and dialysate liquid through the filter, which is provided with a semi-permeable membrane separating the blood from the dialysate liquid. The first circuit is provided with a container, known as a drip chamber, into which the blood is supplied from a first tract of the first circuit, and drips and collects on the bottom of the container, thence to enter a second tract of the first circuit.

The container has the function of preventing air from becoming trapped in the blood in the form of bubbles, which might cause embolisms once the treated blood is returned to the cardiovascular system of the patient. To guarantee the safest possible treatment the blood level in the container must be maintained within an optimum range of values, below which the possibility of creating air bubbles in the blood returning to the patient exists, and above which the pressure increases to unacceptable values which are dangerous for the patient. Thus, the ability to monitor pressure in such a setting is critical to a proper, safe, and successful dialysis treatment.

One type of dialysis application is disclosed in U.S. Pat. No. 6,695,806, entitled "Artificial Kidney Set with Electronic Key," which issued to Gefland et al on Feb. 24, 2004 and is incorporated herein by reference. Another type of dialysis application is disclosed in U.S. Pat. No. 6,887,214, entitled "Blood Pump Having a Disposable Blood Passage Cartridge with Integrated Pressure Sensors," which issued to Levin et al on May 3, 2005 and is incorporated herein by reference. It can be appreciated that U.S. Pat. Nos. 6,695,806 and 6,887,214 are referenced herein for general background and edification purposes only and are not considered limiting features of the embodiments described herein.

Dialysis machines historically have utilized sets of disposable components that are assembled from various parts produced by different manufacturers. This allowed flexibility, but also resulted in certain disadvantages. Joints between component parts, for example, may leak, allow ingress of air and facilitate blood clotting. A high skill was required by hospital nurses and technicians to assemble the tubes, connectors, filters and accessories and then load them correctly into pumps, bubble detectors, pressures sensors and other elements of a dialysis machine. In the setting of a chronic dialysis center such practices were acceptable. In an acute setting, however, such an Intensive Care Unit (ICU) of a hospital, the complexities of dialysis machines can become an impediment.

As a result, the use of mechanical fluid removal in the ICU, emergency rooms and general floors of a hospital has been limited. Some manufacturers have released sophisticated dialysis equipment based on the use of an integrated set of disposable dialysis components in which the tubing, filter and accessories are bonded together and no assembly is required. In such a device, the filter, sensor interfaces and four dedicated pump segments (for blood, dialysate, replacement solution and effluent) can be mounted on a flat plastic cartridge to simplify the loading of the dialysis pumps. Such a dialysis system has been marketed as offering an integrated system for continuous fluid management and automated renal replacement therapy blood.

While such devices do offer significant advantages, such equipment also has a number of deficiencies. One deficiency is that although such systems provide for a set of disposable dialysis components that are continuous and bonded together, the system does not present a smooth blood path, but incorporates elements that create stagnant and slow moving blood zones. In such blood zones clots are likely to form. Such devices may also employ an interface to pressure sensors that is relatively inaccurate, unreliable and requires maintenance. There is thus a need for an improved design of the blood flow dialysis set that is simple to use, requires no maintenance or special training, and also has an improved performance over existing sets of disposable components utilized in such dialysis machines.

Additionally, such dialysis machines do not integrate pressure sensors. Instead, these types of dialysis devices integrate pressure "pods" shaped as domes. The interface surface of a pod can be made from a silicon membrane approximately one inch in diameter. When mounted on such a dialysis machine, the pods interface with the permanently installed pressure sensors that form a part of the machine. The interface is sealed by a rubber gasket so that the pod membrane serves as a lid on the pressure transducer cavity. When in operation, blood and other fluids flow through the pods and come in contact with the membrane.

Pressure pods provide a means to measure the pressure of blood and other fluids flowing outside an interface surface. When the pressure inside the pod is increased, the diaphragm stretches and thereby compresses the air inside a transducer cavity. As a result, pressure in the bloodline or a fluid line can be measured. The pod membrane serves as a barrier between the blood and potential contamination from the environment, as is similar to the clinical invasive vascular blood pressure measurements. This method, although functional, has several deficiencies.

First, to be accurate such pods need to be positioned perfectly when the pressure inside is atmospheric. Over time, if there is even a miniscule leak on the transducer side of the membrane, the pod will creep and gradually stop transmitting pressure accurately because of the tension in the membrane. Second, stretchable membranes and air filled transducer cavities add compliance to the circuit. Compliance is a delay in a pressure measurement due to the time required to stretch the pods and compress the air inside the pod cavity. Compliance is not desired since it makes the system less responsive to controls.

Third, pods filled with blood increase the blood-plastic contact surface and create stagnant zones with low blood flow velocity that facilitate clot formation. Because the clots may form in the pods, the use of pods also necessitates the use of clot capture devices. Fourth, pod domes have a significant volume that increases the time that blood spends in contact with foreign materials. Altogether this increases the risk of blood loss, hypotension and clotting.

In order to address the needs of fluid removal and dialysis in acute emergency settings and to eliminate significant limitations of existing designs, it is believed that an improved sensor system should be adapted for use with dialysis machines. It is believed that the improved multiple sensor system disclosed herein can address these and other continuing needs.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensor system.

It another aspect of the present invention to provide for an improved pressure sensor system for use in dialysis applications.

It is yet another aspect of the present invention to provide for a sensor system that avoids the need for both careful mechanical alignment and electrical connection between the sensor and dialysis machine. A further aspect of the present invention is to provide for a reduced sensor size that permits reduced contact volume and dead-space in a sensing application.

The aforementioned aspects and other objectives and advantages can now be achieved as described herein. A sensor system for dialysis applications is disclosed, which includes a plurality of passive resonant circuit pressure sensors inductively coupled to a plurality of antennas. Wherein each sensor among the plurality of pressure sensors is implemented as inductive-capacitive (LC) resonant circuit (tank) sensors associated with a respective antenna among the plurality of antennas for the wireless transmission of pressure data. A dialysis machine is generally connected to the plurality of pressure sensors and the plurality of antennas, wherein the plurality of pressure sensors monitors pressure during a dialysis operation of the dialysis machine to generate pressure data that is wirelessly transmitted from at least one antenna among the plurality of antennas.

A plurality of oscillator circuits is also associated with the plurality of pressure sensors and the plurality of antennas. Additionally, a plurality of low frequency switches is associated with the plurality of oscillator circuits. An electronics processing module is also provided for processing the pressure data generated by one or more of the pressure sensors, while each oscillator circuit among the plurality of oscillator circuits can be implemented as a Grid Dip Oscillator (GDO). Each GDO can be configured to include an oscillator component that produces an AC output signal that is input to a level shifter, which in turn produces an output signal that has either the negative or positive signal peak clamped to a fixed reference level. This signal is then input to a low-pass filter, which in turn produces a DC output signal. The DC output signal from the filter is thus proportional to the peak-to-peak signal from the oscillator. In this way the use of RF switch is avoided for multiple sensor concepts.

Each antenna can be provided as a planar coil surrounded by a shielding ring. The shielding ring can be configured in the form of metalized plastic with an electrical connection to ground within the dialysis machine. Each pressure sensor can be implemented as an LC tank sensor and can be located in at least one of the following positions within the dialysis machine: an arterial line, a dialyzer line, or a venous line, depending upon design considerations. Each sensor may operate within different resonant frequency bands from one another or within the same or overlapping frequency bands, depending on design goals and considerations.

An alternative embodiment involves the use of wireless LC tank multiple sensors in the context of a sensor system in which the sensors share a single antenna. Multiple capacitors, each of which forms a variable C component in the LC tank sensor, can be linked with a single planar coil, such that each associated variable capacitor results in a pressure dependent signature frequency (i.e., spurs). Multiple frequencies can exist in such a system through prudent design. The amplitudes of the spurs can be maximized for ease of detection.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
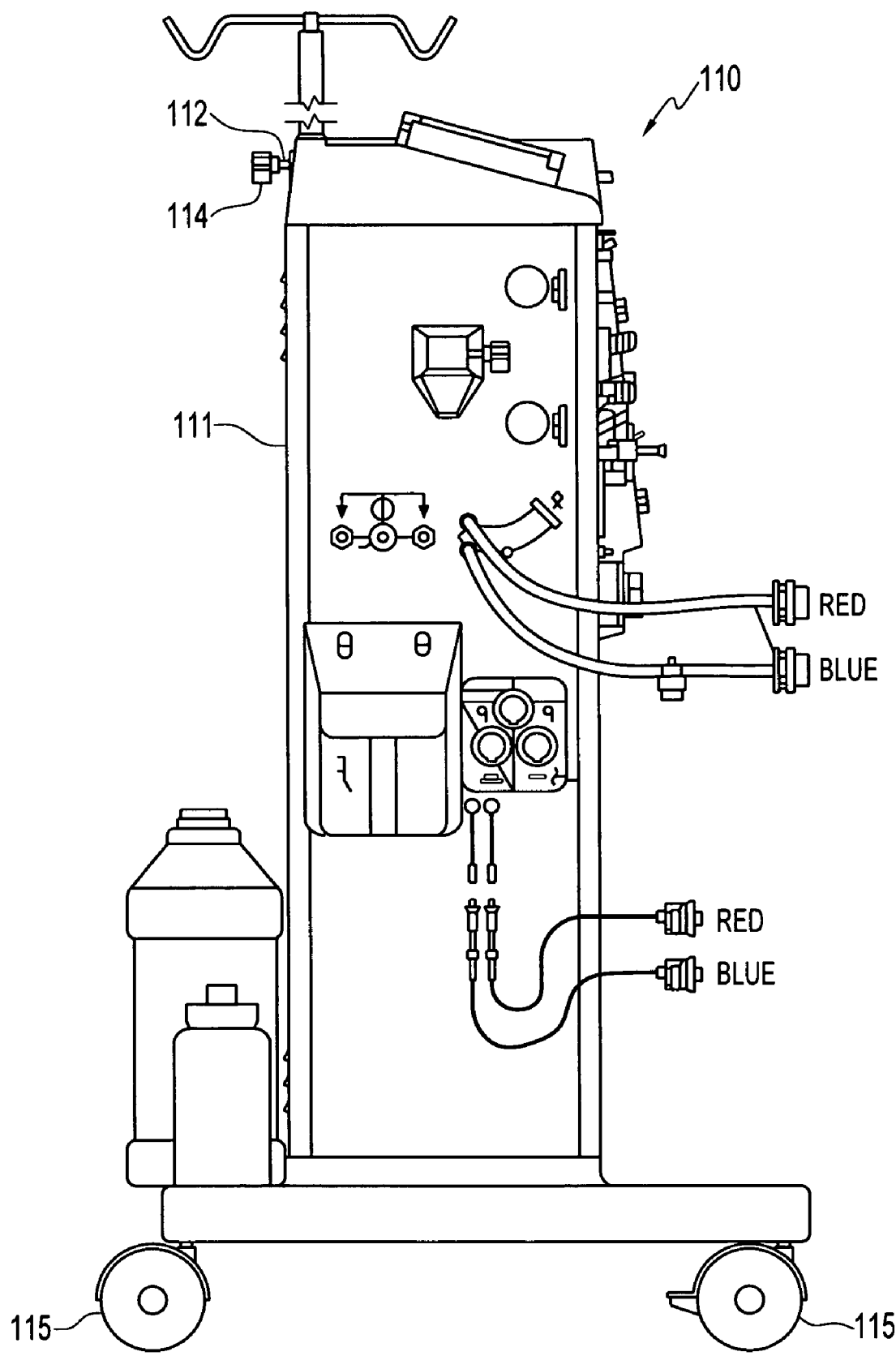
FIG. 1 illustrates a high-level view of the left side of a conventional kidney dialysis machine, which can be adapted for use in accordance with one or more embodiments.

FIG. 1 illustrates a high-level view of the left side of a conventional kidney dialysis machine 110, which can be adapted for use in accordance with one or more embodiments. The dialysis machine 110 generally includes a machine housing 111 that contains a membrane apparatus (not shown) for performing dialysis. The illustrated dialysis machine 110 can also include a threaded shaft 112 extending from the back of the housing 111. The shaft 112 can be located near the top of the housing and a knob 114 can be threaded on the shaft 112.

The housing is generally mounted on wheels 115 that support the housing on the floor of a patient station. It can be appreciated that the dialysis machine 110 depicted in FIG. 1 represents one of many possible dialysis machines that can be utilized in accordance with the embodiments disclosed herein. As such, the dialysis machine 110 illustrated in FIG. 1 is not considered a limiting feature of the disclosed embodiments. Rather, dialysis machine 110 is presented for general edification and exemplary purposes only. It can be appreciated that the embodiments disclosed herein can be practiced not only in the context of dialysis applications, but also in the context of non-dialysis applications, such as, for example, external blood treatment applications.

Figure 2A:
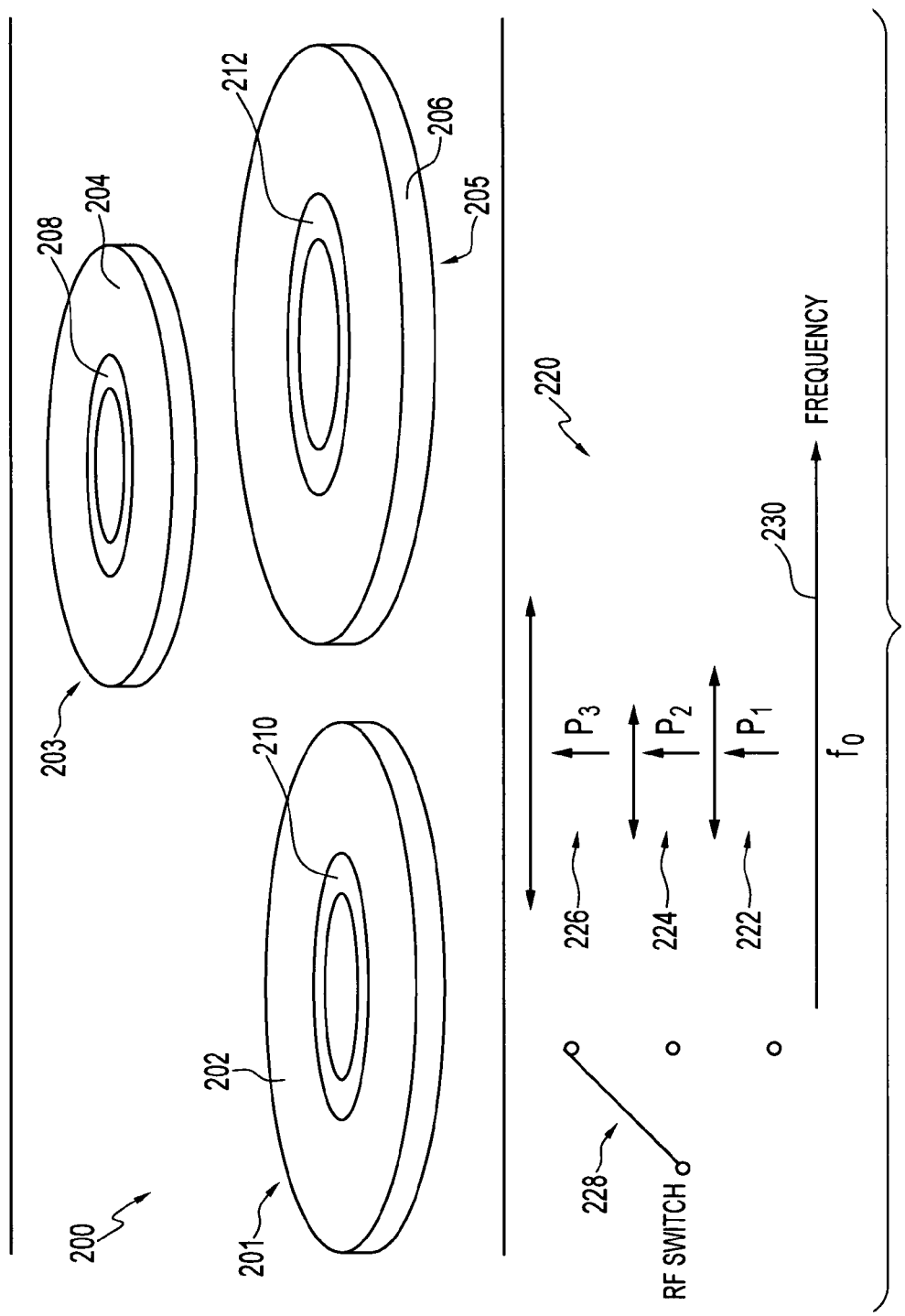
FIG. 2(a) illustrates a system of reader antennas reader antenna, which can operate in overlapping frequency bands about the same 'zero pressure differential' resonant frequency, $f_0$, in accordance with a first embodiment.

FIG. 2(a) illustrates a system 200 of antenna 201, 203, 205, which can operate at the same zero pressure resonant frequency, $f_0$, in accordance with a first possible embodiment. System 200 depicted in FIG. 2(a) can be adapted for use with the dialysis machine 110 depicted in FIG. 1. Sensors (not shown in FIG. 2(a), but illustrated in FIGS. 3, 5 and 6) can be implemented as LC tank sensors in association with system 200 with either L varying with pressure or C or both L and C varying with pressure depending upon design considerations. Such sensors are illustrated in greater detail herein with respect to FIGS. 3–6.

In the configuration of system 200, shielding rings 202, 204, 206 respectively surround and screen one side of one or more of the coil antennas 210, 208, and 212. When utilized in the context of a system that includes a Radio Frequency (RF) switch 228, the set of three antennas 201, 203, 205 can make use of the same frequency range for sensing applications. A graph 220 depicted in FIG. 2(a) illustrates a representative x-ordinate frequency range. In graph 220, a central zero pressure frequency $f_0$ is shown with pressure values 222, 224, and 226 (i.e., $P_1$, $P_2$, $P_3$) varying the resonant frequency associated with three different sensors. Thus, FIG. 2 illustrates detection of resonant frequencies about a common zero-pressure frequency using multiple interrogation coil antenna 210, 208, 212.

Figure 2B:
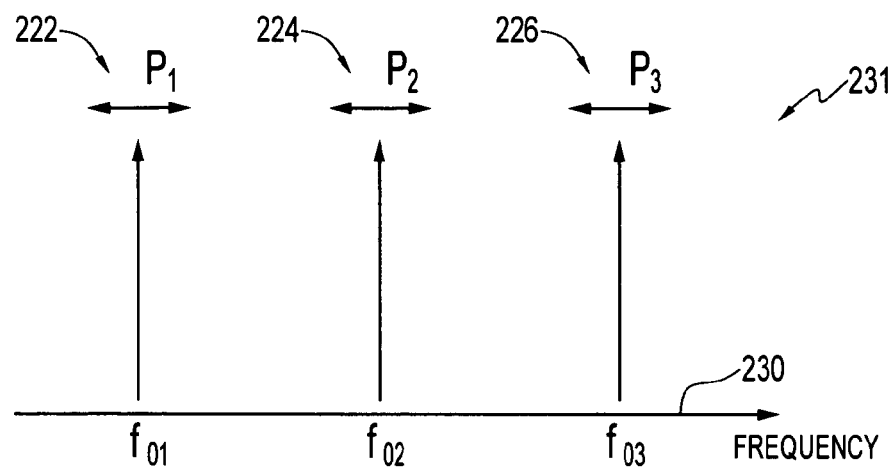
FIG. 2(b) illustrates a graph depicting how the system illustrated in FIG. 2(a), can operate at different resonant frequencies, in accordance with an alternative version of the first embodiment.

FIG. 2(b) illustrates a graph 231 depicting how a system of sensors (e.g., see sensors 402, 404, 406 in FIGS. 5-6 and sensors 330, 344 in FIG. 3) can operate in different resonant frequency bands, in accordance with an alternative version of the first embodiment. Note that in FIGS. 2(a)–2(b) identical or similar elements or components are generally indicated by identical reference numerals. Thus, zero pressure frequencies, $f_0$, $f_{02}$, and $f_{03}$ are shown along the x-ordinate frequency range 230 in FIG. 2(b).

FIG. 2(b) indicates that multiple LC tank sensors can operate in different resonant frequency bands to avoid interference between different sensor and antenna signals. Single or multiple interrogation electronics, such as, for example, Grid Dip Oscillator (GDO) circuits, can be utilized depending on the available dynamic range of the GDO circuit. In other words, GDO circuits can be utilized if the frequency range over which the oscillator circuit operates can sustain oscillations. In either case, single or multiple antenna configurations can be implemented, depending on the strength of the inductive coupling of each of the sensors to the antenna(s). The embodiment depicted in graph 220 of FIG. 2(a) uses sensors operating in the same frequency resonant frequency band and multiple interrogation antenna 201, 203, 205 separated from one another and preferably with the respective shielding 202, 204, 206 around each coil 210, 208, 212.

Note that the RF signal from the antenna coils 210, 208, 212 can be focused and/or limited to respective sensors directly facing the antenna, while signals radiated to other sensors not directly facing the antenna coil can be completely shielded or significantly reduced. Where necessary RF switches such as RF switch 228 depicted in FIG. 1 can be used to switch the supply and/or output signals from utilized GDO circuits.

Assuming that it is desired to implement a system in which the sensors operate within different frequency bands (e.g., see graph 231 of FIG. 2(b)); one or more GDO circuits should be utilized, which operate over the widest range frequencies. Such a configuration can be implemented with a single antenna coil and a GDO with a wide dynamic range. In order to obtain the detection sensitivity required, however, the change in resonant frequency of a single sensor (i.e., with pressure) may already reach the limits of the GDO's dynamic range. Thus, multiple antennas with multiple GDO circuits may be required. Alternatively, where sensors operate within the same frequency band, multiple antennas may also be required to physically differentiate between the sensors (e.g., see FIG. 2(a)).

Each antenna coil 210, 208, 212 can take the form of a planar coil based, for example, on a Printed Circuit Board (PCB) or polymer substrate, or the form of a multi-layer PCB coil, wound Litz wire, wound copper wire, or other similar structure. Shielding can be implemented in, for example, metalized plastic or sheet metal, with electrical connections to ground in the dialysis equipment of, for example, the dialysis machine 110 depicted in FIG. 1. Preferably, this shielding would be implemented in the same process as the coil manufacture itself. Alternatively, a material with high permeability could be attached, deposited and/or located nearby, such as, for example, mu-metal, in order to stop or reduce the field due to limited skin depth at measurement frequencies. The diameter and height of the shielding rings 202, 204, and/or 206 can be determined by the relative distance and the angle between sensors and their respective antenna coils 210, 208, 212.

In the embodiments described above wherein the GDO dynamic range is large enough, multiple sensors can be connected to one GDO with three different antennas. In such a scenario, an RF switch such as, for example, RF switch 228 depicted in FIG. 2(a), can be utilized to switch between the interrogation antennas 201, 203, 205. In embodiments where the dynamic range of the GDO is limited, multiple GDO circuits can be linked to a single antenna using an RF switch. Alternatively, wherein both multiple GDO circuits and antenna are required to provide both the required operating frequency range and coupling between sensors that are spatially separated along with their respective antenna, two different arrangements can be implemented, as indicated herein with respect to FIGS. 5 and 6, which are described in greater detail below.

Figure 4:
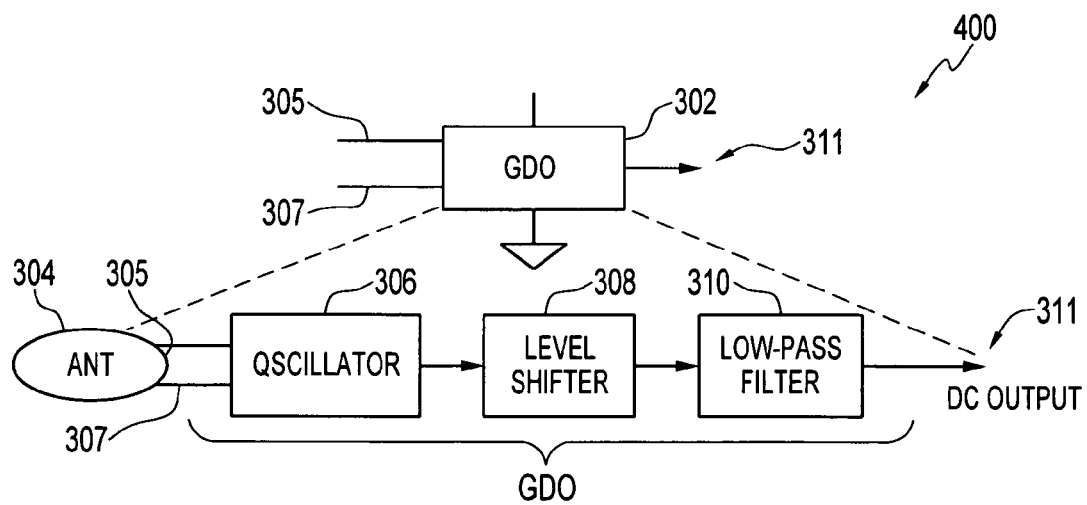
FIG. 4 illustrates a block diagram depicting components that can be utilized to implement an example oscillator circuit in accordance with an alternative, but first embodiment.
Figure 3:
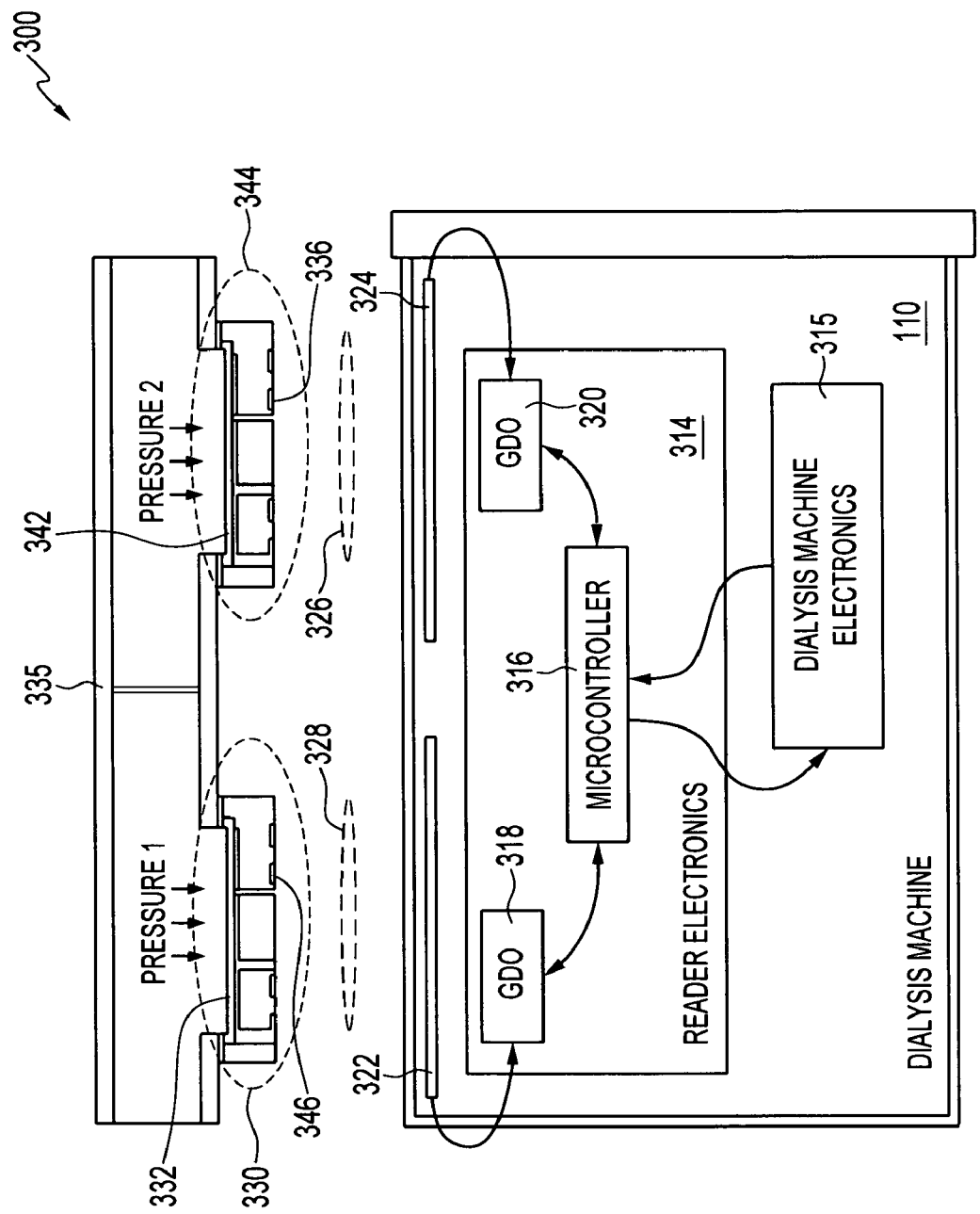
FIG. 3 illustrates a block diagram depicting a sensor system, which can be implemented in accordance with a preferred embodiment.
Figure 5:
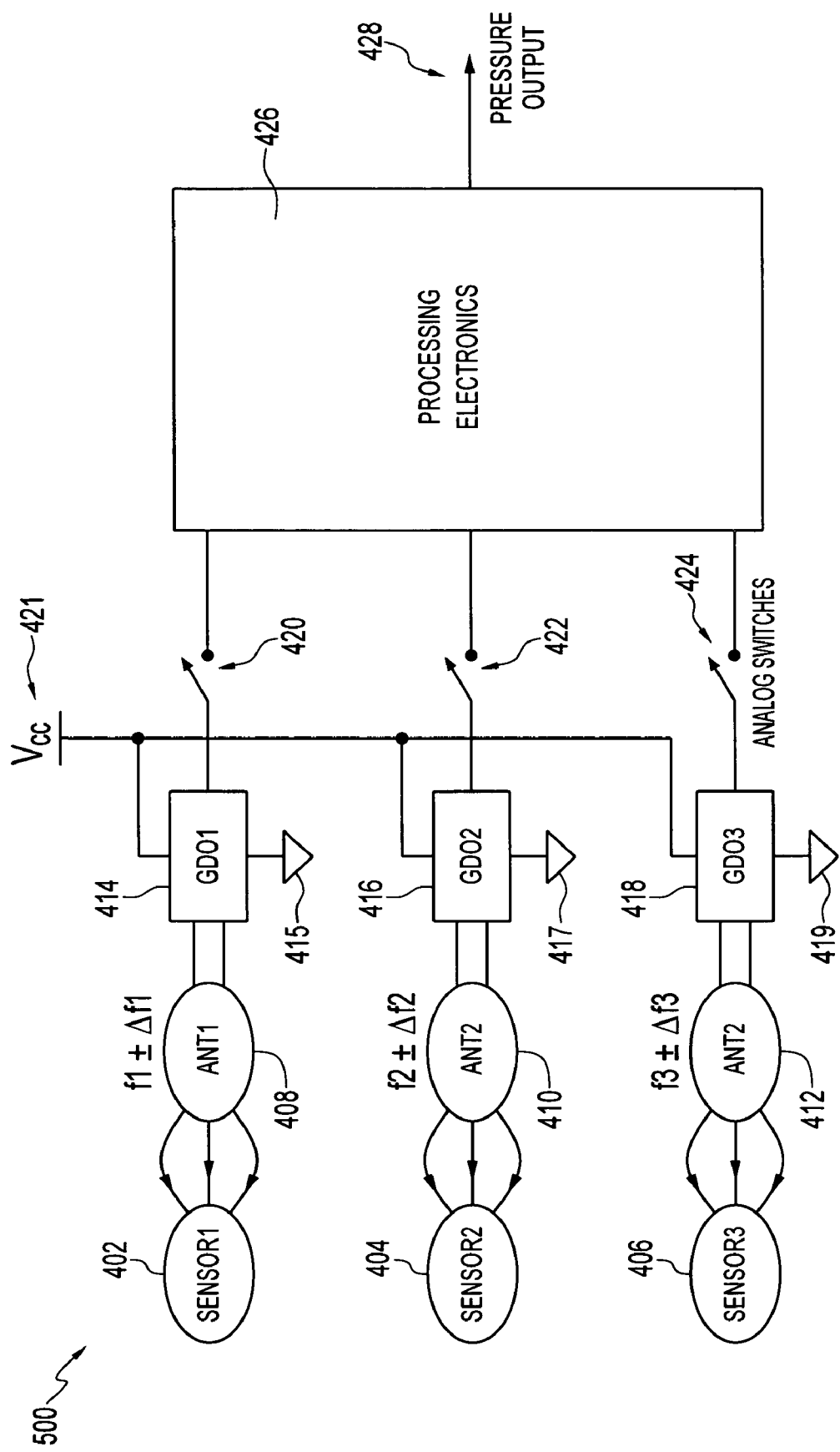
FIG. 5 illustrates a block diagram of a multiple sensor system for use in dialysis applications, in accordance with an alternative first embodiment.
Figure 6:
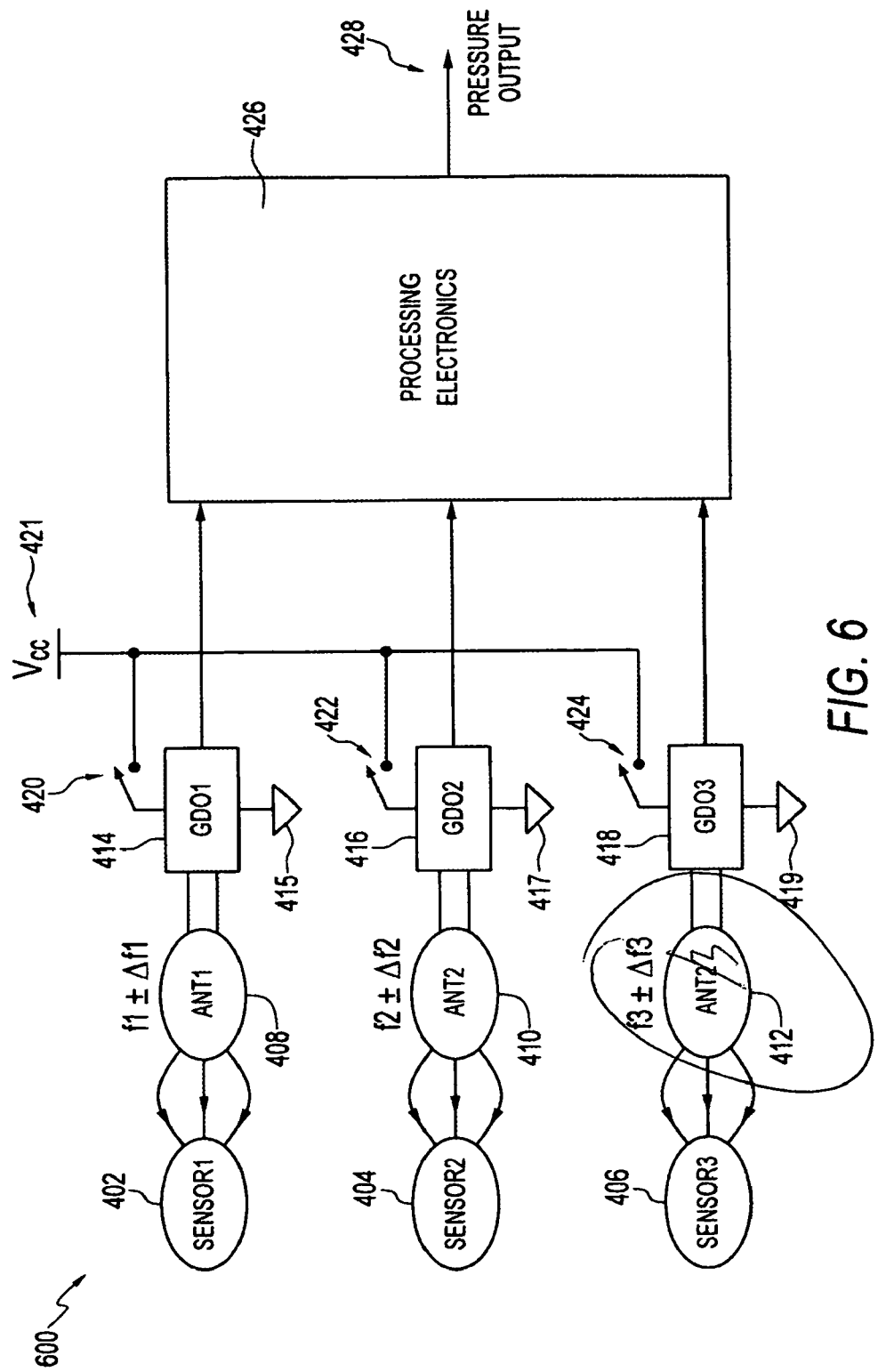
FIG. 6 illustrates a block diagram of a multiple sensor system for use in dialysis applications, in accordance with another version of the embodiment depicted in FIG. 5.

FIG. 3 illustrates a block diagram depicting a sensor system 300, which can be implemented in accordance with a preferred embodiment and in association with the antenna embodiments depicted in FIGS. 1–2(a)/(b) and FIGS. 4–6. System 300 generally incorporates the use of multiple wireless LC tank pressure sensors for use with a hemodialysis machine such as, for example, the dialysis machine 110 depicted in FIG. 1. System 300 includes a disposable cartridge 335 which can support one or more pressure sensors 330, 344. The pressure sensor 330 includes a variable capacitance sensing element 332 and a sensor coil 346. Similarly, the pressure sensor 344 includes a sensing element 342 and a sensor coil 336. Inductive coupling (electromagnetic field show schematically as 328 and 326) are also provided, wherein the primary inductive coupling is between the sensor coils 346 and 336 and reader coils 322 and 324 respectively.

The dialysis machine 110 can also include reader coils 322 and 324, which are located respectively proximate to the sensor coils 346 and 336. Importantly the relative position of the sensor and reader coils need not be precisely maintained in order to achieve wireless transfer of pressure data, thus allowing ease of placement and attachment of the disposable cartridge by the hospital nurses and technicians. The dialysis machine 110 can also incorporate various measurement and control electronics 315 which communicate with reader electronics 314 that include a GDO 318, a GDO 320 and a microcontroller 316. Note that each GDO 318, 320 are respectively similar to the GDO 400 illustrated in FIG. 4. The system 300 is illustrated as a two sensor configuration. It can be appreciated, however, that system 300 can be modified to operate with additional sensors, GDO circuits, and so forth.

FIG. 4 illustrates a block diagram depicting components that can be utilized to implement an example oscillator circuit 302 in accordance with an alternative, but first embodiment. Note that in FIGS. 4, 5 and 6, the illustrated configurations generally depict a DC/low frequency switch arrangement. FIGS. 5–6 generally relate to a three sensor configuration. It can be appreciated, however, that the system 300 depicted in FIG. 3 can be modified to operate in the context of a three sensor configuration, such as that depicted in FIGS. 5–6, rather than the two sensor configuration of FIG. 3. The oscillator circuit or GDO 302 is generally composed of an oscillator 306, which in turn generates AC signal that is sent to a level shifter 308. The level shifter 308 ensures the signal from oscillator is available to the low-pass filter 310 without the influence of the DC bias voltage of the oscillator circuit 302 and also that the output signal has either the negative or positive signal peak clamped to a reference level. The signal strength may be further increased by using a peak detector circuit (not shown) and output to the low pass filter 310. The low-pass filter 310 finally generates a DC output 311 which is thus proportional to the peak-to-peak signal from the oscillator circuit 302. The GDO 302 can be connected to an antenna 304 via connecting lines 305, 307.

Note that the antenna 304 depicted in FIG. 4 is analogous to each of the antenna 201, 203, 205 depicted in FIG. 2(a). In other words, one or more GDO circuits can be implemented in association with one or more antennas 201, 203, 205, depending upon design considerations. Note that as utilized herein, the term "oscillator" may refer to the GDO or GDO circuit itself or may simply refer to the oscillator component, such as component 306, which makes up one portion of the overall GDO, such as, for example, GDO 302. Sensors 402, 404, 406 and can be implemented by LC tank sensors, depending upon design considerations.

FIG. 5 illustrates a block diagram of a multiple sensor system 500 for use in dialysis applications, in accordance with an alternative first embodiment. System 500 includes multiple GDO circuits 414, 416, 418 (i.e., respectively, GDO1, GDO2, GDO3). Each GDO 414, 416, 418 is analogous to the GDO 302 depicted in FIG. 4. GDO 414 is connected to a first antenna 408, which in turn is inductively coupled to a first sensor 402. GDO 416 is connected to a second antenna 410, which in turn is inductively coupled to a second sensor 404. GDO 418 is connected to a third antenna 412, which in turn is inductively coupled to a third antenna 406. GDO 414 is also connected to ground 415 and to a voltage supply 421. GDO 416 is connected to ground 417 and also to the voltage supply 421. Similarly, GDO 418 is connected to ground 419 and to voltage supply 421. The antennas 408, 410 and 412 are analogous to the antennas 201, 203, 205 depicted in FIG. 2(a).

GDO 414 is also connected to a low frequency switch 420, which in turn can in a closed position permit an electrical connection of GDO 414 to a processing electronics module 426. Similarly, GDO 416 is connected to a low frequency switch 422, which in turn can in a closed position permit an electrical connection of GDO 416 to the processing electronics module 426. Likewise, GDO 418 can be connected to a low frequency switch 424, which in turn can in a closed position permit an electrical connection of GDO 418 to the processing electronics module 426. Note that a pressure output signal 428 can be obtained from the processing electronics module 426. It is also significant to note that each of the low frequency switches 420, 422, and 424 can be in some embodiments, perform an analogous function to the RF switch 228 depicted in FIG. 2(a).

In system 500, multiple GDO circuits 414, 416, 418 are utilized. Both the GDO circuits 414, 416, 418 and the antenna 408, 410, 412 are always powered up (i.e., oscillations continuously set up in the circuit and antenna). One or more low frequency switches 420, 422, 424 can be operated by the processing electronics 426, forming a multiplexer to select the output from each sensor in turn.

In the configuration depicted in FIG. 5, three separate GDO circuits 414, 416, 418 are respectively associated with three separate sensors 402, 404, 406. The three GDO circuits 414, 416, and 418 share the processing electronics module 426. The output from each GDO 414, 416, 418 can comprise a DC voltage. Thus, the resulting multiplexer can be composed of low frequency switches 420, 422, 424, which are simple in structure and typically are of a low cost. It can be appreciated that although only three sensors 402, 404, 406 and three GDO circuits 414, 416, 418 along with three antenna 408, 410, 412 are depicted in FIG. 4, alternative embodiments with more or fewer such sensors, antenna or GDO components may be implemented, depending upon the sensing application requirements.

Sensors 402, 404, 406 depicted in FIGS. 5–6 and sensors 330, 344 depicted in FIG. 3 can be implemented for example as inductance-capacitance resonant circuit (LC tank) sensors such as those disclosed in U.S. patent application Ser. No. 11/242,271, entitled "Wireless Pressure Sensor and Method Forming the Same." Alternatively, such pressure sensors can be implemented as wireless capacitance pressure sensors, such as those described in U.S. patent application Ser. No. 11/226,085, entitled "Wireless Capacitance Pressure Sensor."

FIG. 6 illustrates a block diagram of a multiple sensor system 600 for use in dialysis applications, in accordance with another version of the embodiment depicted in FIG. 5. Note that in FIGS. 5–6, identical or similar parts or elements are generally indicated by identical reference numerals. System 600 is similar to system 500 depicted in FIG. 5, with some variations to the overall circuit structure. In the configuration depicted in FIG. 6, the switches 420, 422, and 424 are respectively located between the voltage supply 421 and respective GDO circuits 414, 416, and 418. Switches 420, 422, and 424 can be implemented as low frequency switches. A GDO can be selected by powering it up in order to ensure that there is no interference from a neighboring GDO. Additionally, the power drawn in the configuration depicted in FIG. 6 may be lower than that of system 500 illustrated in FIG. 5.

In system 600 depicted in FIG. 6 the GDO circuits 414, 416, 418 can be powered up in turn by the processing electronics 426, thereby removing or reducing interference between the antenna 408, 410, 412. The response time of system 600 is however reduced based on the need for the GDO circuits 414, 416, and/or 418 to warm-up (i.e., time for oscillations in the GDO's LC oscillator circuit to build up to their full amplitude).

The various first embodiments of FIGS. 1–6 solve the need for multiple wireless pressure sensor systems for hemodialysis applications. Between three and six sensors, for example, can be utilized to make up the whole range of pressures and locations for use in a dialysis machine, such as the dialysis machine 110 depicted in FIG. 1. Such sensors can be located on the arterial line (i.e., after blood out of patient, before blood pump), the dialyzer line (i.e., after blood pump, before dialyzer), and/or on the venous line (i.e., after dialyzer, before patient), or any of a number of other possible locations on or in association with a dialysis machine or another medical application, such as, for example, external blood treatment or separation applications.

The typical pressure range over which such sensors (e.g., sensors 402, 404, 406 of FIGS. 5–6) preferably (although not necessarily) operate is between −700 mmHg and +1000 mmHg. This is, of course, only a suggested range and other ranges are also possible, depending upon design considerations and specific application requirements.

In general, size limitations for sensors utilized in hemodialysis applications are problematic. It would be beneficial to design a multiple-sensor system with the lowest cost, small size and fewest parts. FIGS. 1–6 represent one possible embodiment. A second embodiment involves the use of wireless LC tank multiple sensors in the context of a sensor system in which the sensors share a single antenna. Multiple capacitors can be linked with a single planar coil, such that each associated variable capacitor results in a signature frequency (i.e., spurs). Multiple characteristic resonant frequencies can be detected in such a system through prudent design.

Figure 7:
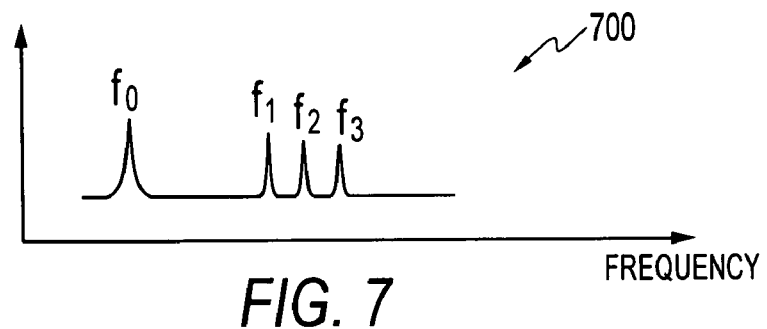
FIG. 7 illustrates a graph depicting a variety of frequencies in the context of a sensor system for dialysis applications, in accordance with a second embodiment.

FIG. 7 illustrates a graph 700 depicting a variety of frequencies in the context of a sensor system for dialysis applications, in accordance with a second embodiment. In graph 700, $f_0$ represents the fundamental frequency of the sensor system that will not be detected, while $f_1$, $f_2$, and $f_3$ are spurs related to each sensor in, for example, the three sensor system.

Figure 8:
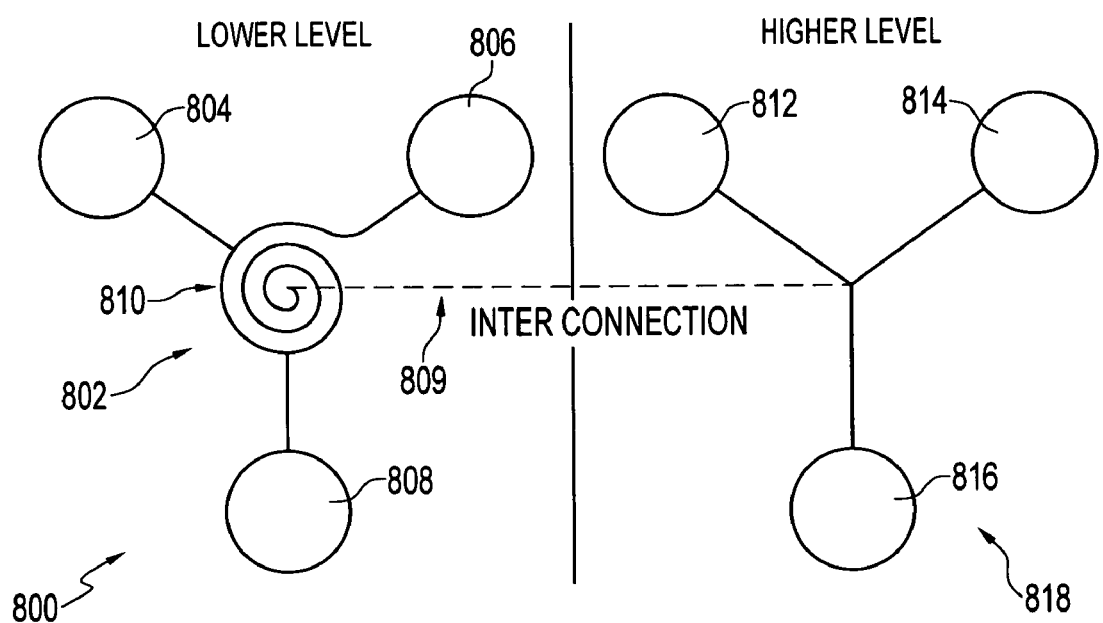
FIG. 8 illustrates a sensor system based on a plurality of circular electrodes forming a plurality of variable capacitors, in accordance with the second embodiment.

FIG. 8 illustrates a sensor system 800 based on a plurality of circular electrodes forming variable capacitors, in accordance with the second embodiment. In the configuration of system 800, two sub-systems 802 and 818 are illustrated. Sub-system 802 includes a group of electrodes 804, 806, 808, while sub-system 818 includes a group of electrodes 812, 814, 816. In the lower level configuration of sub-system 802, the three circular electrodes 804, 806, and 808 can be associated with three respective variable capacitors (not shown in FIG. 8). Each electrode 804, 806, and 808 is connected to an antenna 810. At the higher level of sub-system 818, the three electrodes 812, 814, 816 can be located on a pressure diaphragm (not shown in FIG. 8) and respectively correspond to each electrode 805, 806, 808 of the lower level of sub-system 802. Note that the dashed line 809 in FIG. 8 represents the interconnection between sub-systems 802 and 818.

Figure 9:
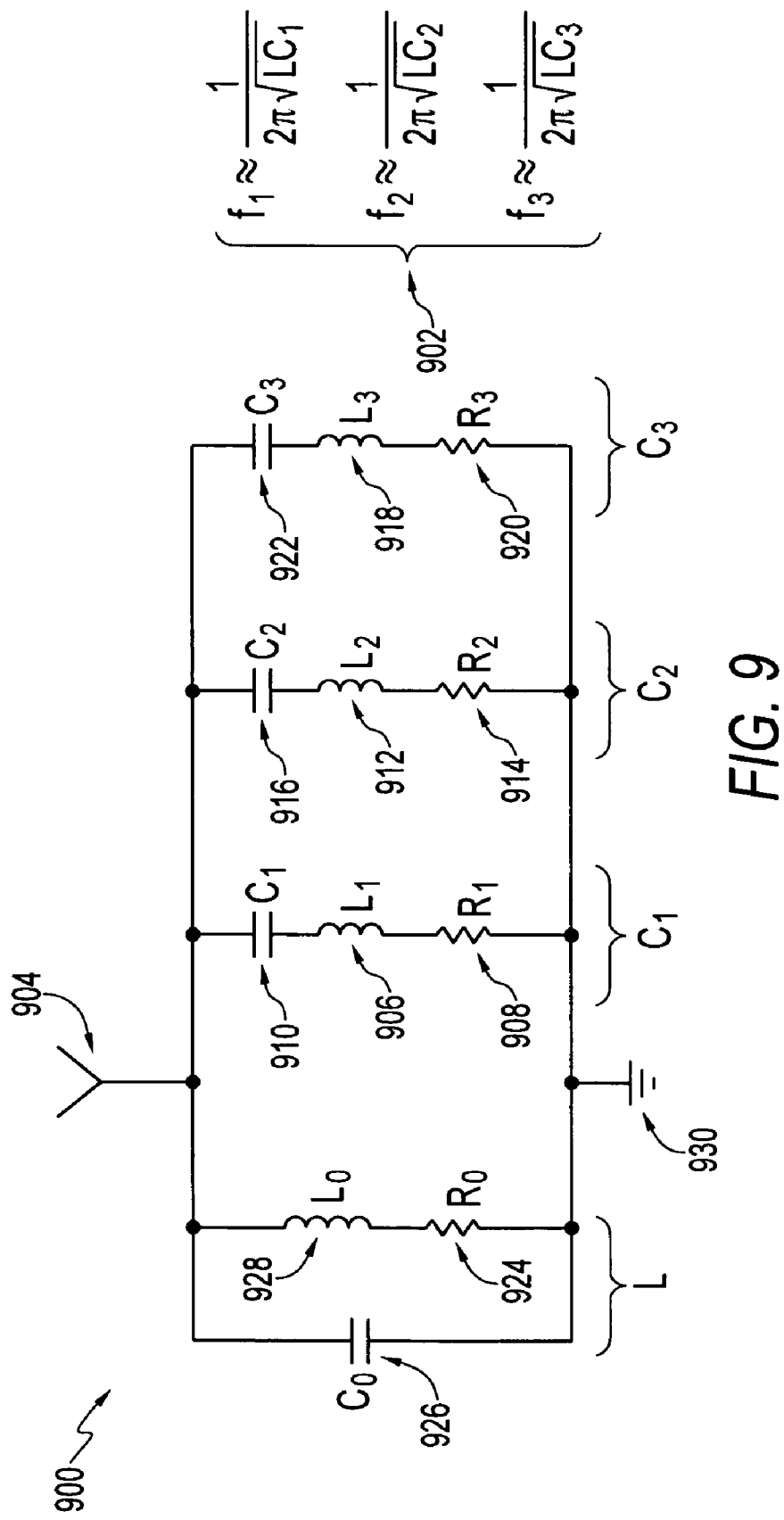
FIG. 9 illustrates a schematic diagram of an example equivalent circuit of the configuration depicted in FIG. 8.

FIG. 9 illustrates a schematic diagram of an example equivalent circuit 900 of the configuration depicted in FIG. 8. The configuration depicted in FIG. 9 is presented in order to assist in explaining the functioning of the configurations depicted in FIG. 7. Note that in FIGS. 7 and 9, the variables $f_1$, $f_2$, and $f_3$ generally represent the same functionality. In FIG. 9, $R_0$, $C_0$, $R_1$, $L_1$, $R_2$, $L_2$, $R_3$ and $L_3$ represent small electrical values. Note that equations 902 depicted in FIG. 9 depicted general formulations for determining $f_1$, $f_2$, and $f_3$. In general, the equivalent circuit 900 can be composed of an inductor 928 connected to a capacitor 926, which in turn is connected to a resistor 924 that in turn can be connected to ground 930. Similarly, a capacitor 910 is connected to a resistor 908, which in turn is connected to an inductor 906 that in turn can be connected to ground 930.

A capacitor 916 can be connected to a resistor 914, which in turn is connector to an inductor 912 that in turn is connected to ground 930. A capacitor 918 can be further connected to a resistor 920 that in turn is connected to an inductor 922. Note that the inductor 928, and the capacitors 910, 916 and 918 are generally connected to an antenna 904. FIGS. 8–9 thus generally indicate that the pressure sensors discussed herein can be implemented in the context of an LC type sensor (e.g., LC (Inductance-Capacitance) tank sensor), an RLC (Resistance-Inductance-Capacitance) type sensor, or a combination thereof, depending upon design considerations.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A sensor system for dialysis applications, comprising:
a plurality of pressure sensors, wherein each pressure sensor among said plurality of pressure sensors comprises an inductive-capacitive tank circuit such that said plurality of pressure sensors is inductively coupled respectively to a plurality of coil antennas for the wireless transmission of pressure data, wherein each coil antenna among said plurality of coil antennas comprises a planar coil surrounded by a shielding ring; and a dialysis machine connected to said plurality of coil antennas, wherein said shielding ring comprises metallized plastic with an electrical connection to a ground located within said dialysis machine and wherein said plurality of pressure sensors monitors pressure during an operation of said dialysis machine to generate pressure data that is wirelessly transmitted to at least one antenna among said plurality of coil antennas.

2. The system of claim 1 further comprising:
a plurality of oscillator circuits associated with said plurality of coil antennas;
a plurality of low frequency switches associated with said plurality of oscillator circuits; and
an electronics module for operating said switches and for processing said pressure data generated by said plurality of pressure sensors.

3. The system of claim 2 wherein each oscillator circuit among said plurality of oscillator circuits comprises a Grip Dip Oscillator (GDO), and said electronics module comprises a microcontroller.

4. The system of claim 3 wherein said GDO comprises an oscillator that produces an output signal that is input to a level shifter, which in turn produces an output signal which is input to a low-pass filter, which in turn produces a DC output signal.

5. The system of claim 1 wherein each pressure sensor among said plurality of pressure sensors operates within a different resonant frequency band.

6. The system of claim 1 wherein each pressure sensor among said plurality of pressure sensors operates within a same or an overlapping resonant frequency band.

7. The system of claim 1 wherein at least one pressure sensor among said plurality of pressure sensors is located in at least one of the following positions within said dialysis machine: an arterial line, a dialyzer line, or a venous line.

8. A sensor system for dialysis applications, comprising:
a plurality of pressure sensors, wherein each pressure sensor among said plurality of pressure sensors comprises at least one of the following types of sensors: an LC (Inductance-Capacitance) type sensor, an RLC (Resistance-Inductance-Capacitance) type sensors or a combination thereof, and wherein each pressure sensor among said plurality of pressure sensors is coupled with at least one antenna for the wireless transmission of pressure data, wherein each antenna among said plurality of antennas comprises a planar coil surrounded by a shielding ring; and
a dialysis machine connected to said antenna, wherein said shielding ring comprises metalized plastic with an electrical connection to a ground located within said dialysis machine and wherein said plurality of pressure sensors monitors pressure during operation of said dialysis machine to generate pressure data that is wirelessly transmitted to said antenna.

9. The system of claim 8 further comprising:
a plurality of oscillator circuits associated with said plurality of pressure sensors and said at least one antenna;
a plurality of low frequency switches associated with said plurality of oscillator circuits; and
an electronics module for controlling a plurality of low frequency switches and for processing a said pressure data generated by said plurality of pressure sensors.

10. The system of claim 9 wherein at least one pressure sensor among said plurality of pressure sensors is located in at least one of the following positions within said dialysis machine: an arterial line, a dialyzer line, or a venous line.

11. A sensor system for dialysis applications, comprising:
a plurality of pressure sensors, wherein each pressure sensor among said plurality of pressure sensors comprises an LC (Inductance-Capacitance) tank sensor and is inductively coupled to a respective antenna among a plurality of antennas for the wireless transmission of pressure data wherein each antenna among said plurality of antennas comprises a planar coil surrounded by a shielding ring;
a dialysis machine connected to said plurality of antennas, wherein said shielding ring comprises metalized with an electrical connection to a round located within said dialysis machine and wherein said plurality of pressure sensors monitors pressure during an operation of said dialysis machine to generate pressure data that is wirelessly transmitted to at least one antenna among said plurality of antennas;
a plurality of oscillator circuits associated with said plurality of antennas;
a plurality of low frequency switches associated with said plurality of oscillator circuits; and
an electronics module for operating said plurality of low frequency switches and processing said pressure data generated by said plurality of pressure sensors.

12. The system of claim 11 wherein each pressure sensor among said plurality of pressure sensors operates within a different resonant frequency band.

13. The system of claim 11 wherein each pressure sensor among said plurality of pressure sensors operates within a same or an overlapping resonant frequency band.

14. The system of claim 11 wherein each oscillator circuit among said plurality of oscillator circuits comprises a GDO.

15. The system of claim 11 wherein at least one pressure sensor among said plurality of pressure sensors is located in at least one of the following positions within said dialysis machine: an arterial line, a dialyzer line, or a venous line.

16. A sensor system for dialysis applications, comprising:
a plurality of pressure sensors, wherein each pressure sensor among said plurality of pressure sensors comprises an inductive-capacitive tank circuit such that said plurality of pressure sensors is inductively coupled respectively to a plurality of coil antennas for the wireless transmission of pressure data; and
a plurality of oscillator circuits associated with said plurality of coil antennas;
a plurality of low frequency switches associated with said plurality of oscillator circuits;
an electronics module for operating said switches and for processing said pressure data generated by said plurality of pressure sensors, wherein each oscillator circuit among said plurality of oscillator circuits comprises a Grip Dip Oscillator (GDO), and said electronics module comprises a microcontroller, wherein said GDO comprises an oscillator that produces an output signal that is input to a level shifter, which in turn produces an output signal which is input to a low-pass filter, which in turn produces a DC output signal; and
a dialysis machine connected to said plurality of coil antennas, wherein said plurality of pressure sensors monitors pressure during an operation of said dialysis machine to generate pressure data that is wirelessly transmitted to at least one antenna among said plurality of coil antennas.

17. The system of claim 16 wherein at least one pressure sensor among said plurality of pressure sensors Is located in an arterial line associated with said dialysis machine.

18. The system of claim 16 wherein at least one pressure among said plurality of pressure sensors is located in a dialyzer line associated with said dialysis machine.

19. The system of claim 16 wherein at least one pressure among said plurality of pressure sensors is located in a venous line associated with said dialysis machine.

20. The system of claim 16 wherein each pressure sensor among said plurality of pressure sensors operates within a different resonant frequency band.

21. The system of claim 16 wherein each pressure sensor among said plurality of pressure sensors operates within a same or an overlapping resonant frequency band.

* * * * *

UNITED STATES PATENT AND TRADEMARK OFFICE
CERTIFICATE OF CORRECTION

PATENT NO. : 7,219,021 B2 Page 1 of 1
APPLICATION NO. : 11/317706
DATED : May 15, 2007
INVENTOR(S) : James Z T Liu et al.

It is certified that error appears in the above-identified patent and that said Letters Patent is hereby corrected as shown below:

In Column 11, line 45, delete "sensors" and add --sensor--;
In Column 12, line 15, after "metalized" add --plastic--;
In Column 12, line 16, delete "round" and add --ground--.

Signed and Sealed this

Sixth Day of November, 2007

JON W. DUDAS
*Director of the United States Patent and Trademark Office*